United States Patent [19]
Emanuel et al.

[11] Patent Number: 5,932,449
[45] Date of Patent: Aug. 3, 1999

[54] DETECTION OF BOTULINUM TOXIN

[75] Inventors: Peter A. Emanuel, Abingdon; James J. Valdes, Churchville; Mohyee E. Eldefrawi, Pikesville; James P. Burans, Bethesda, all of Md.

[73] Assignee: The United States of America as represented by the Secretary of the Army, Washington, D.C.

[21] Appl. No.: 08/792,824

[22] Filed: Jan. 30, 1997

Related U.S. Application Data

[60] Provisional application No. 60/011,013, Feb. 1, 1996.

[51] Int. Cl.$^6$ .................................................. C12P 21/04
[52] U.S. Cl. ..................... 435/70.1; 536/23.53; 435/69.1; 435/69.6; 530/387.1; 530/388.4; 530/389.5

[58] Field of Search ................... 536/23.1, 23.53; 435/69.1, 69.6, 70.1, 70.21, 340, 326, 328, 320.1; 935/22, 66–75; 530/387.1, 388.4, 359.5, 866

[56] References Cited

FOREIGN PATENT DOCUMENTS 15982  6/1995  WIPO .

*Primary Examiner*—Sheela Huff
*Attorney, Agent, or Firm*—Ulysses John Biffoni

[57] ABSTRACT

Recombinant antibody fragments (rFabs) specific to botulinum types A and B toxin complexes are provided. These rFabs are useful as immunosensors for detecting botulinum toxin in food, health care, and military applications. The DNA sequences coding for the rFabs are also disclosed.

31 Claims, No Drawings

DETECTION OF BOTULINUM TOXIN

This application is a nonprovisional continuation of provisional application Ser. No. 60/011,013, filed Feb. 1, 1996.

GOVERNMENTAL INTEREST

The invention described herein may be manufactured, used and licensed by or for the U.S. Government.

FIELD OF THE INVENTION

The present invention relates generally to the detection of *Clostridium botulinum*. More specifically, the present invention relates to recombinant antibody fragments (rFabs) specific to botulinum types A and B toxin complexes. These rFabs are useful as immunosensors for detecting botulinum toxin in food, health care, and military applications, and may have therapeutic potential.

BACKGROUND OF THE INVENTION

The sole cause of flaccid paralysis in the food poisoning disease known as botulism is a neurotoxin (NT) of approximately 150 kDa, which is produced as antigenically distinct serotypes (types A, B, C, D, E, F and G) by certain strains of *Clostridium botulinum*, *C. butyricum*, and *C. barrati*. In contaminated food, as well as in bacterial culture, the NT is noncovalently associated with non-neurotoxic proteins (non-NTs) in a large, up to 900 kDa, and stable complex. These non-NTs may and may not have hemagglutinating activity and are often immunologically related. For example, type A non-NTs have potent hemaglutinating activity and the non-NTs from type A and B complexes are serologically cross-reactive.

Botulinum toxin complexes, primarily a mixture of types A and B, are also used in biological weapons. Because of the harmful effect such weapons could have on the health of military personnel and civilian populations, as well as the potential for contracting food poisoning from botulinum-contaminated food, there is a need for quick and inexpensive detection of the presence of botulinum toxin type A and/or B in air, water, and food samples.

SUMMARY OF THE INVENTION

Accordingly, it is an object of the present invention to provide an immunosensor for the detection of biological weapons grade botulinum toxin.

Another object of the present invention is to provide an immunosensor that is specific for the non-NT, or hemagglutinating, components of both type A and B toxoids.

Another object of the present invention is to provide such an immunosensor which is rapidly and economically produced.

These and other objects are satisfied by the present invention which is directed to anti-type A and B non-NT rFab fragments (hereinafter anti-AB rFabs) expressed by recombinant bacteria and the use of these anti-AB rFabs for detecting botulinum toxin type A and/or B in air, water, and food samples. The recombinant bacteria were isolated from a recombinant antibody library made using known techniques.

In brief, a cDNA library was made from mouse messenger RNA (mRNA) isolated from the spleens of mice immunized with human pentavalent toxoid emulsified in FCA. The cloned mouse heavy and light chain genes were expressed in *Escherichia coli* phage display libraries as heavy and light chain polypeptides which associate together to form rFab antibody fragments. This combinatorial library was screened against botulinum type B complex to enrich the library for non-NT specific clones. The clones which produced anti-AB rFabs of the invention were then isolated from the enriched library and the DNA sequences of the light and heavy chain coding regions were determined.

DETAILED DESCRIPTION OF THE INVENTION

The present invention provides anti-AB rFabs, amino acid sequences thereof, nucleotide sequences coding for said amino acid sequences, recombinant expression vectors containing said nucleotide sequences, and recombinant microorganisms containing said vectors. The anti-AB rFabs of the invention were isolated as described in detail below.

EXAMPLE 1

Toxin Preparations

Botulinum toxin type A complex (500 kDa) and type B complex (500 kDa) were purchased from WAKO BioProducts (Richmond, Va.). The type A and type B neurotoxins (each 150 kDa) were isolated from liquid bacterial culture according to published methods (Sathyamoorthy, V. and DasGupta, B. R., Separation, purification, partial characterization and comparison of the heavy and light chains of botulinum neurotoxins types A, B, and E, J. of Biol. Chem., Vol. 260 (19), pp. 10461–10466 (1985), incorporated herein by reference). The isolated NTs were judged pure by SDS-PAGE and amino acid sequence determinations. Toxoid of the type B complex was prepared as reported elsewhere. (Sugiyama, H., DasGupta, B. R. and Ohishi, I. Disulfide-immunogenicity relationship of botulinal toxins., Proc. of the Soc. for Exper. Biol. and Med., Vol. 145, pp. 1306–1309 (1974), incorporated herein by reference).

EXAMPLE 2

Mouse Immunization Protocol for Recombinant Antibodies

Five, female BALB/c mice were immunized subcutaneously with 0.25 ml of pentavalent botulinum toxoid types A, B, C, D, and E (Michigan Department of Public Health), emulsified in 1 part by volume Complete Freund's Adjuvant (CFA, Difco, Detroit, Mich.). The mice were subsequently boosted three times at 17 day intervals with 0.25 ml of pentavalent vaccine emulsified in 1 part Incomplete Freund's Adjuvant (IFA). Five days after the last immunization, the mice were immunized with 50 µg of toxoid of botulinum type B complex in IFA. The mice were then primed with an intravenous injection of 100 µl of botulinum toxin B complex at 2 ng/ml, which also contained 100 µg of botulinum toxoid type B complex. Mice were killed and spleens removed 3 days after priming immunization. Sera from these animals were pooled and analyzed by direct ELISA, described below, for titer to botulinum toxin type A and B complexes, with an endpoint titer of 1:100,000.

EXAMPLE 3

Anti-Botulinum Toxin Direct ELISA

Direct ELISA assays were performed using 96 well microtiter plates (Immulon II, Dynatech, Chantilly, Va.). The plates were coated overnight at 4° C. with 100 µl of specified botulinum toxin at 2 μg/ml of phosphate buffered saline (PBS 0.01M phosphate buffer, 0.15M NaCl, pH 7.4, Sigma, St. Louis, Mo.) and with bovine serum albumin at the same concentration as the negative antigen. Botulinum type B toxin complex or botulinum type B NT were used as antigens in assays to characterize the specificity of recombinant Fabs. The plates were then washed 6 times using an automated plate washer with PBS Wash Buffer (PBS, 0.1% Tween 20, 0.1% thimerosal, pH=7.4).

Sera diluted in ELISA Dilution Buffer (5% Dry Skim Milk, 0.1% Tween 20, 0.001% thimerosal, PBS pH=7.4) was added to alternating wells of the ELISA plates containing specified botulinum toxin and negative BSA antigen and were incubated for 1 h at 37° C. The plates were then washed again as before with ELISA wash buffer.

Horseradish peroxidase (HRP)-conjugated goat anti-mouse (Kirkegaard and Perry Laboratories, Inc, Gaithersburg, Md.) or anti-Fab (Accurate Chemical & Scientific Corp., Westbury, N.Y.) antibody diluted 1:2500 in ELISA Dilution buffer was added to each well of the ELISA plates and incubated for one hour at 37° C. The plates were washed again 6 times with PBS wash buffer.

ABTS substrate (Kirkegaard and Perry Laboratories, Inc.) was added to each well and incubated for one hour at 37° C. The optical density (OD) at 405 nm of each well of the ELISA plate was determined using an ELISA plate reader (Dynatech). An adjusted OD was obtained by subtracting the OD of the reaction of the antibody or Fab with the negative antigen (BSA) from the OD of the reaction of the antibody solution to the positive antigen. The positive cutoff for this assay was calculated from the adjusted OD of the mean plus three standard deviations of three negative controls consisting of culture media without Fab or monoclonal antibodies or botulinum antibody negative mouse sera.

The polyclonal serum was shown to be responsive towards botulinum toxin complex serotypes A and B (>500 kDa), with an endpoint titer of 1:100,000, as well as towards pure botulinum NT B (150 kDa), that lacked the hemagglutinin commonly found associated with the toxin complex. From the ELISA data, it was concluded that the challenged mice had raised an immune response directed against the 150 kDa NT B as well as towards the non-NT proteins of the toxin complex.

EXAMPLE 4

First Strand cDNA Synthesis and PCR Amplification

Total RNA was isolated from the spleens of a second set of mice immunized as described in Example 2. The isolation procedure was essentially that described by Chomczynski, P. and Sacchi, N., Single step method of RNA isolation by acid guanidinium thiocyanate-phenol-chloroform extraction, Anal. Biochem., Vol. 162, pp. 156–159 (1987), incorporated herein by reference. Twenty micrograms of the isolated RNA was allowed to anneal with either oligo-dT$_{18}$ or heavy chain specific immunoglobulin primers, and then extended with 80 units of RNAse H⁻ MMLV reverse transcriptase (Stratagene, Inc., LaJolla, Calif.) and 1 mM dNTPs. The resulting cDNAs were processed and amplified essentially as described by Hogrefe, H. and Shopes, B., Construction of Phagemid Display Libraries with PCR-amplified Immuno-globulin Sequences, PCR Methods Appl. S109–S122 (1994) (incorporated herein by reference), in order to isolate individual sets of immunoglobulin genes by PCR amplification.

EXAMPLE 5

Construction of Primary Lambda Library

Heavy and light chain PCR fragments were subjected to digestion with Sfi I overnight at 50° C. The digested chains were gel purified and 1 μg of each set were ligated together in a final volume of 10 μl containing 5 units T4 DNA ligase (Life Technologies, Inc., Gaithersburg, Md.). Two identical ligations were pooled, phenol extracted, ether extracted, and ethanol precipitated. The pellet was resuspended in water and subjected to digestion with 100 units each of Spe I and Not I (Boehringer-Mannheim, Indianapolis, Ind.) overnight at 37° C. The resulting mixture of 1.4 kb inserts was gel isolated in 10 μl of water. Forty ng of the Fab gene insert mixture was ligated into Not I/Spe I digested SurfZAP™ λ arms (Stratagene) essentially as described by Amberg, J., Hogrefe, H. H., et al., SuZAP™ Vector: Linking Phenotype to Genotype for Phagemid Display Libraries, Strategies Mol. Biol., Vol. 5, pp. 2–5 and Vol. 6 (1), pp. 2–4, each of which is incorporated herein by reference. See also Hogrefe, H., Mullinax, R., Lovejoy, A., Hay, B., and Sorge, J., A bacteriophage lambda vector for the cloning and expression of immunoglobulin Fab fragments on the surface of filamentous phage, Gene Vol. 128, pp. 119–126 (1993); Hogrefe, H., Amberg, J., Hay, B., Sorge, J. and Shopes, B., Cloning in bacteriophage lambda vector for the display of binding proteins on filamentous phage, Gene, Vol. 137, pp. 85–91 (1993), each of which is incorporated herein by reference. The recombinant arms were then packaged into lambda virus (Kretz, P. L., Effect of lambda packaging extract mcr restriction activity on DNA cloning, Nucleic Acids Res., Vol. 17 (13), p. 5409 (1989) incorporated herein by reference). The primary lambda library was titered on XL-1 Blue cells and then amplified using the plate lysate amplification technique (Sambrook, J., Fritsch, E., et al., Molecular Cloning: A Laboratory Manual, Cold Spring Harbor Laboratory Press (1989), incorporated herein by reference).

EXAMPLE 6

Production of Phage for Bio-Panning

The resulting primary lambda library was then subjected to mass excision by infection with ExAssist™ helper phage (Stratagene) in the presence of XL-1 Blue cells (Hay, B. and Short, J. M., ExAssist™ helper phage and SOLR™ cells for Lambda ZAP® II excisions, Strategies Molec. Biol., Vol. 5 (1), pp. 16–18 (1992), herein incorporated by reference). The excised double stranded recombinant pSurfscript™ phagemid were amplified in SOLR™ cells in LB broth, containing 100 μg/ml carbenecillin and 50 μg/ml kanamycin (LB$^{Carb/Kan}$ broth), and allowed to amplify for 6 hours at 37° C.

The cells were harvested, resuspended in 10 mM MgSO$_4$, and 1×10$^9$ SOLR™ cells were mixed with 9×10$^9$ pfu of VSCM13 helper phage for 15 min. at 37° C. The culture was then diluted to an OD$_{600}$=0.1 with LB$^{Carb/Kan}$ broth and shaken at 30° C. overnight. The culture was centrifuged and the supernatant containing the bacteriophage was precipitated with polyethylene glycol 8000 (PEG). (See McCafferty, J., Griffiths, A. D., et al., Phage Antibodies: filamentous phage displaying antibody variable domains, Nature, Vol. 348, pp. 552–554 (1990), incorporated herein by reference). The pellet was resuspended in 1 ml of TE and reprecipitated with PEG. The resulting bacteriophage pellet was resuspended in 100 μl of TE/0.1% BSA.

Co-infection of the cells with the VCSM13 helper virus induced production of filamentous bacteriophage that express the heavy and light chain polypeptides on the surface of the virus. (See Parmley, S. F. and Smith, G. P., Antibody-selectable filamentous fd phage vectors: affinity purification of target genes, Gene 73, 305–318 (1988), incorporated herein by reference). The display of the rFabs on the surface of the phage allowed for the enrichment of antigen specific clones through biopanning against botulinum type B complex or type B NT immobilized in the wells of microtiter plates as described below.

EXAMPLE 7

Bio-Panning Enrichment and Rescue of Positive Clones

The biopanning procedure used was a modification of two protocols (Persson, M., Caothien, R., and Burton, D., Generation of diverse high affinity human monoclonal antibodies by repertoire cloning, Proc. Natl. Acad. Sci., Vol. 88, pp. 2432–2436 (1991), incorporated herein by reference, and Hogrefe and Shopes (1994)). The wells of Nunc 96 well Immuno-plates were coated for 2 hours at 4° C. with 100 µl of 10 µg/ml botulinum type B complex or type B NT in 100 mM sodium bicarbonate buffer, pH=9.0. The plates were then blocked with 1% BSA, 0.5% Tween-20, in PBS (blocking buffer) for 30 minutes at 25° C., followed by three washes with 0.5% Tween-20/PBS (wash buffer).

Approximately $2 \times 10^{10}$ cfu phagemid were added to each well and the wells were then incubated for 2 hours at 4° C. Unbound phagemids were removed by washing once with wash buffer. To avoid the loss of rare clones the first round of biopanning was washed only once and subsequent rounds were washed two and ten times. The bound phagemids were eluted by adding 100 µl of 100 mM glycine/0.5% BSA, pH=2.5, to the well and incubating for 10 minutes at 25° C. The elution mix was then mixed briefly and neutralized with 2M Tris base, pH=12.

Eluted phage were used to infect XL-1 Blue cells and the sample was diluted with $LB^{Carb}$ and shaken for 1 h at 37° C. VCSM13 helper phage ($1 \times 10^{10}$ pfu) and 50 µg/ml kanamycin were added and the culture shaken overnight at 29° C. The phagemids were collected as above and the biopanning was repeated for a total of three rounds of selection.

EXAMPLE 8

Colony Lift Hybridization

Following the final round of enrichment, the positive colonies were duplicate plated on $LB^{Carb}$ plates, using wetted nitrocellulose filters overlaid onto the bacterial plates. One set of colonies growing directly on the nitrocellulose filters was lysed in a sealed chamber containing a ¼ inch layer of chloroform on the bottom. The filters were submerged in lysozyme buffer (50 mM Tris, pH=8.0, 150 mM NaCl, 5 mM $MgCl_2$, 3% BSA, 400 µg/ml lysozyme, and 1 U/ml DNase I). After 1 hour at 25° C., the filters were transferred to a fresh bath of lysozyme for an additional hour, then washed twice for 10 minutes each, in TBST (20 mM Tris, pH=7.5, 150 mM NaCl, 0.05% Tween-20) and blocked for one hour in blocking solution (1% BSA, 20 mM Tris, 150 mM NaCl). Finally, the filters were transferred to 125 ml of blocking solution to which 160 µl of 200 nM $^{125}$I-labeled botulinum type B toxin complex (ICN Industries, Irvine, Calif.) or $^{125}$I-labeled type B NT had been added. (Toxins were labeled using the Chloramine T method and unbound $^{125}$I was removed by gel filtration on a Sephadex G-10 column run in 0.05M acetic acid, 0.2M NaCl, 0.3% BSA.)

After 1.5 hours at 25° C., the unbound labeled antigen was removed by six 10 minute washes with TBST. The filters were then air dried on blotting paper and exposed to autoradiograph film for 4 hours. Re-alignment of labeled colonies with the master plate allowed the identification of numerous bacterial clones which expressed antibodies capable of binding antigen, i.e., botulinum type B toxin complex or type B NT. Positive clones were subcloned into the pHist purification vector (Tera Biotechnology, LaJolla, Calif.) as described below.

EXAMPLE 9

Subcloning Into pHist and Purification of Fabs

The recombinant pSurfscript™ phagemids were cleaved with Not I/Spe I and the excised Fab gene inserts were recovered in preparative scale in a 2% TAE gel (Amberg, J. et al. (1993); Hogrefe et al. 1994). The purified inserts were then ligated into the pHist vector cut with Not I/Spe I. pHist, a modified version of pSurfscript, has a linker encoding six histidines inserted in place of the cpIII gene. Bacteria cells (e.g., XL-1 Blue or JM105) transformed with pHist 5 express a rFab comprising a light chain polypeptide and a heavy chain polypeptide fused with a histidine hexapeptide tail. The majority of the expressed rFab is trapped in the periplasmic space with small amounts of the rFab being released into the media upon cell death and lysis.

A Ni-NTA resin (Nickle-Nitrolotriacetate) which binds histidine oligomers with high affinity was used to purify the rFab proteins from sonicated cell extracts of induced clones by affinity chromatography according to the manufacturer (Qiagen, Chatsworth, Calif.). See also Lindner, P., B. Guth, et al., Purification of native proteins from the cytoplasm and periplasm of Escherichia coli using IMAC and histidine tails: A comparison of proteins and protocols, Methods: Companion Methods Enzymol. Vol. 4, p. 2, incorporated herein by reference. Antibody protein was eluted from the resin under non-reducing conditions with 500 mM imidazole. This purification with metal chelate affinity chromatography resulted in highly purified rFabs at levels between 500 and 1600 µg/liter of LB broth (data not shown).

A number of the purified rFabs were analyzed by SDS-PAGE. One clone, pHist5, produced a rFab, named BotFab 5, which migrated as a 50 kDa protein under non-reducing conditions and as two polypeptides of 31 and 29 kDa under reducing conditions (data not shown). Probing a western blot of the SDS-PAGE gel run under non-reducing conditions with mouse anti-Fab antiserum confirmed that the 50 kDa BotFab 5 polypeptide was mouse Fab (data not shown).

EXAMPLE 10

Characterization of Antibody Specificity Towards Botulinum Toxin

Overnight cultures of positive clones were grown and induced with 1 mM isopropyl β-D-thiogalactopyranoside (IPTG) when in early log phase. The cells were pelleted and 100 ul of the supernatant was allowed to bind for 1 hour to microtiter plates that had been coated with 100 ul of 5 ug/ml botulinum type A or B complex, type A or B NT, or bovine serum albumin (BSA) as a negative control. The plates were blocked and washed as described above. The wells were then probed with 100 ul of goat anti-mouse Fab-HRP conjugate, which served as a secondary calorimetric probe. The conjugate, allowed to bind for 2 hours, was developed after 6 wash cycles by adding ABTS substrate (2'-azino-bis-3-thylbenthiazoline-6-sulphonate) to each well and then incubating for one hour at 37° C. The optical density (OD) at 405 nm of each well of the ELISA plate was determined using an ELISA plate reader (Dynatech). The results of several representative rFab clones are presented in Table 1 below:

TABLE 1

| rFab Name | Type A Complex | Type B Complex | Type A NT | Type B NT | BSA |
|---|---|---|---|---|---|
| BotFab 1 | 1.85 | 2.70 | 0.03 | 0.03 | 0.33 |
| BotFab 5 | 0.62 | 1.40 | 0.04 | 0.07 | 0.05 |
| BotFab 7 | 2.08 | 2.80 | 0.05 | 0.05 | 0.05 |
| BotFab 8 | 1.73 | 2.40 | 0.09 | 0.07 | 0.09 |
| BotFab 11 | 0.07 | 0.07 | 0.04 | 0.04 | 0.04 |
| BotFab 12 | 1.35 | 2.05 | 0.04 | 0.05 | 0.06 |
| ToxFab 146 | 0.03 | 0.03 | 0.02 | 1.41 | 0.03 |
| ToxFab 149 | 0.04 | 0.03 | 0.02 | 1.06 | 0.02 |
| ToxFab 150 | 0.03 | 0.03 | 0.02 | 0.07 | 0.03 |

Data are O.D. units at 405 nm which are not normalized for protein concentration.

As shown by the data in Table 1, rFabs produced by clones isolated after biopanning the λ library against botulinum type B complex, including BotFab 5, were shown by ELISA to be reactive to botulinum types A and B toxin complexes and not reactive to the 150 kDa NT of type A or B. As noted above, the non-NT proteins in the botulinum toxin complexes A and B are immunologically related. Similarly, rFabs produced by clones isolated after biopanning and enriching against the Type B NT were specific to the Type B NT and did not cross-react with Type A NT or the toxin complexes.

Several clones which expressed anti-AB rFabs were selected for DNA sequence analysis. The DNA sequence of the pHist 5 construct is shown in SEQ ID NO:1. The Fab gene insert is separately set forth in SEQ ID NO:2. Nucleotides 117–827 code for the light chain polypeptide and nucleotides 847–1611 code for the heavy chain polypeptide of BotFab 5. Similarly, the DNA sequences of the Fab gene inserts in pHist 1, pHist 20, and pHist 22, which code for BotFab 1, 20, and 22, respectively, are shown in SEQ ID NOS:5, 8, and 11, respectively. The pHist 5 recombinant construct has been deposited with the American Type Culture Collection (Rockville, Md.) as Accession Number 98316 on Feb. 7, 1997. pHist 5 provides the framework for creating other clones. (pHist 1, 20, & 22).

The amino acid sequences of the light and heavy chain polypeptides for each of these constructs were deduced using the DNA STRIDER program (free software available on the Internet) and are shown in SEQ ID NOS:3–4 (BotFab 5), SEQ ID NOS:6–7 (BotFab 1), SEQ ID NOS:9–10 (BotFab 20), and SEQ ID NOS:12–13 (BotFab 22). A comparison of these sequences shows that they contain large stretches of highly homologous regions, suggesting these rFabs all bind to the same non-NT epitope in the types A and B complexes.

Thus, the invention not only includes rFabs containing the recited amino acid sequences of SEQ ID NOS:3–4, 6–7, 9–10, and 12–13, it also includes other rFabs capable of specifically binding to the same epitope. Those rFabs embraced by the invention can be readily determined using commercially available protein folding programs which predict the structure of BotFab 5 and its epitope binding site as well as what changes can be made to its amino acid sequence without changing the binding site. Such rFabs are defined as those having an amino acid sequence with at least 90% homology to the light and heavy chain amino acid sequences of BotFab 5, the preferred rFab of the invention.

The invention also embraces all isolated and purified DNA fragments with DNA sequences coding for the light and heavy chain amino acid sequences of BotFabs 5, 1, 20, and 22. Thus, the invention includes DNA fragments comprising the coding portions of SEQ ID NOS:2, 5, 8, and 11, or their complementary sequences, and DNA fragments containing DNA sequences which are substantially homologous to the coding portions of SEQ ID NOS:2, 5, 8 and 11 or their complementary sequences.

Substantially homologous DNA sequences are defined as having at least about 85% homology over the defined length of the DNA sequences, with at least about 90% homology being preferred and at least about 95% homology being most preferred. Sequences that are substantially homologous may be identified in a Southern hybridization experiment under stringent conditions. Defining stringent conditions for a particular hybridization experiment is within the skill of the art. Generally, hybridization under stringent conditions is performed at about 5° C. lower than the thermal melting point for the specific sequence at a defined ionic strength and pH (T. Maniatis et al., Molecular Cloning, A Laboratory Manual, Cold Spring Harbor Laboratory (1982), pp. 387–389, incorporated herein by reference). Typical stringent conditions include hybridization in 4×SSC at 65° C. or in 4×SSC, 50% formamide at 42° C., followed by washing in 0.1×SSC at 65° for 30 min.

The DNA fragments according to the invention may be cloned into bacterial expression vectors well-known in the art to generate recombinant expression vectors capable of producing anti-AB rFabs. Preferably, the rFab vectors contain a DNA sequence coding for a purification tail to allow for purification of the expressed rFab by affinity chromatography.

The expression vectors include known transcriptional and translational control elements operatively linked to the light and heavy chain genes. Preferably, such control elements will allow expression of the rFabs in more than one type of microorganism.

The rFabs of the invention, particularly BotFab 5, offer several advantages over monoclonal antibodies for routine testing of biological samples for the presence of botulinum complexes. First, the Fabs are less expensive to produce since they may be isolated from large scale bacterial cultures rather than hybridoma cultures. Also, the affinity of a Fab is more easily altered using known techniques, e.g., by in vitro mutagenesis of its gene and subsequent screening of the expressed Fabs.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention. For example, given the sequences disclosed herein, one skilled in the art is capable of combining the light chain coding gene from one pHist construct with the heavy chain coding gene from another phist construct to produce a recombinant construct capable of expressing an anti-AB rFab. Also, nucleotide sequences coding for any known purification tags, including the histidine tail, may be fused to either the light or heavy chain genes.

We claim:

1. A purified and isolated recombinant antibody fragment (rFab) comprising a light chain polypeptide and a heavy chain polypeptide, each of said polypeptides having an N-terminus and a carboxyl terminus, wherein said light chain polypeptide consists of the amino acid sequence of SEQ ID NO:3 and said heavy chain polypeptide consists of the amino acid sequence of SEQ ID NO:4, and wherein said rFab is capable of binding specifically to the non-neurotoxin component of a botulinum neurotoxin complex selected from the group consisting of type A and type B.

2. The rFab of claim 1, further comprising a six amino acid histidine tail fused to said carboxyl terminus of said heavy chain polypeptide.

3. A purified and isolated DNA fragment encoding an amino acid sequence for a recombinant antibody fragment, said antibody fragment comprising a light chain polypeptide and a heavy chain polypeptide, wherein the light chain polypeptide consists of the amino acid sequence of SEQ ID NO:3 and the heavy chain polypeptide consists of the amino acid sequence of SEQ ID NO:4, and wherein said purified and isolated DNA fragment comprises a first DNA sequence coding for the light chain polypeptide and a second DNA sequence coding for the heavy chain polypeptide.

4. The DNA fragment of claim 3, wherein said first DNA sequence comprises nucleotides 117–827 of SEQ ID NO:2 and said second DNA sequence comprises nucleotides 847–1611 of SEQ ID NO:2.

5. The DNA fragment of claim 4, further comprising a third DNA sequence located between said first and second DNA sequences, said third DNA sequence consisting of nucleotides 828–846 of SEQ ID NO:2.

6. The DNA fragment of claim 3, wherein said first DNA sequence comprises the complementary sequence of nucleotides 117–827 of SEQ ID NO:2 and said second DNA sequence comprises the complementary sequence of nucleotides 847–1611 of SEQ ID NO:2.

7. The DNA fragment of claim 6, further comprising a third DNA sequence located between said first and second DNA sequences, said third DNA sequence consisting of nucleotides 828–846 of SEQ ID NO:2.

8. A purified and isolated recombinant antibody fragment (rFab) comprising a light chain polypeptide and a heavy chain polypeptide, each of said polypeptides having an N-terminus and a carboxyl terminus, wherein said light chain polypeptide consists of the amino acid sequence of SEQ ID NO:6 and said heavy chain polypeptide consists of the amino acid sequence of SEQ ID NO:7, and wherein said rFab is capable of binding specifically to the non-neurotoxin component of a botulinum neurotoxin complex selected from the group consisting of type A and type B.

9. The rFab of claim 8, further comprising a six amino acid histidine tail fused to said carboxyl terminus of said heavy chain polypeptide.

10. A purified and isolated DNA fragment encoding an amino acid sequence for a recombinant antibody fragment, said antibody fragment comprising a light chain polypeptide and a heavy chain polypeptide, wherein said light chain polypeptide consists of the amino acid sequence of SEQ ID NO:6 and the heavy chain polypeptide consists of the amino acid sequence of SEQ ID NO:7, and wherein said purified and isolated DNA fragment comprises a first DNA sequence coding for the light chain polypeptide and a second DNA sequence coding for the heavy chain polypeptide.

11. The DNA fragment of claim 10, wherein said first DNA sequence comprises nucleotides 87–788 of SEQ ID NO:5 and said second DNA sequence comprises nucleotides 815–1579 of SEQ ID NO:5.

12. The DNA fragment of claim 11, further comprising a third DNA sequence located between said first and second DNA sequences, said third DNA sequence consisting of nucleotides 789–814 of SEQ ID NO:5.

13. The DNA fragment of claim 10, wherein said first DNA sequence comprises the complementary sequence of nucleotides 87–788 of SEQ ID NO:5 and said second DNA sequence comprises the complementary sequence of nucleotides 815–1579 of SEQ ID NO:5.

14. The DNA fragment of claim 13, further comprising a third DNA sequence located between said first and second DNA sequences, said third DNA sequence consisting of nucleotides 789–814 of SEQ ID NO:5.

15. A purified and isolated recombinant antibody fragment (rFab) comprising a light chain polypeptide and a heavy chain polypeptide, each of said polypeptides having an N-terminus and a carboxyl terminus, wherein said light chain polypeptide consists of the amino acid sequence of SEQ ID NO:9 and said heavy chain polypeptide consists of the amino acid sequence of SEQ ID NO:10, and wherein said rFab is capable of binding specifically to the non-neurotoxin component of a botulinum neurotoxin complex selected from the group consisting of type A and type B.

16. The rFab of claim 15, further comprising a six amino acid histidine tail fused to said carboxyl terminus of said heavy chain polypeptide.

17. A purified and isolated DNA fragment encoding an amino acid sequence for a recombinant antibody fragment, said antibody fragment comprising a light chain polypeptide and a heavy chain polypeptide, wherein said light chain polypeptide consists of the amino acid sequence of SEQ ID NO:9 and the heavy chain polypeptide consists of the amino acid sequence of SEQ ID NO:10, and wherein said purified and isolated DNA fragment comprises a first DNA sequence coding for the light chain polypeptide and a second DNA sequence coding for the heavy chain polypeptide.

18. The DNA fragment of claim 17, wherein said first DNA sequence comprises nucleotides 88–798 of SEQ ID NO:8 and said second DNA sequence comprises nucleotides 818–1582 of SEQ ID NO:8.

19. The DNA fragment of claim 18, further comprising a third DNA sequence located between said first and second DNA sequences, said third DNA sequence consisting of nucleotides 799–817 of SEQ ID NO:8.

20. The DNA fragment of claim 17, wherein said first DNA sequence comprises the complementary sequence of nucleotides 88–798 of SEQ ID NO:8 and said second DNA sequence comprises the complementary sequence of nucleotides 818–1582 of SEQ ID NO:8.

21. The DNA fragment of claim 20, further comprising a third DNA sequence located between said first and second DNA sequences, said third DNA sequence consisting of nucleotides 799–817 of SEQ ID NO:8.

22. A purified and isolated recombinant antibody fragment (rFab) comprising a light chain polypeptide and a heavy chain polypeptide, each of said polypeptides having an N-terminus and a carboxyl terminus, wherein said light chain polypeptide consists of the amino acid sequence of SEQ ID NO:12 and said heavy chain polypeptide consists of the amino acid sequence of SEQ ID NO:13, and wherein said rFab is capable of binding specifically to the non-neurotoxin component of a botulinum neurotoxin complex selected from the group consisting of type A and type B.

23. The rFab of claim 22, further comprising a six amino acid histidine tail fused to said carboxyl terminus of said heavy chain polypeptide.

24. A purified and isolated DNA fragment encoding an amino acid sequence for a recombinant antibody fragment, said antibody fragment comprising a light chain polypeptide and a heavy chain polypeptide, wherein said light chain polypeptide consists of the amino acid sequence of SEQ ID NO:12 and the heavy chain polypeptide consists of the amino acid sequence of SEQ ID NO:13, and wherein said purified and isolated DNA fragment comprises a first DNA sequence coding for the light chain polypeptide and a second DNA sequence coding for the heavy chain polypeptide.

25. The DNA fragment of claim 24, wherein said first DNA sequence comprises nucleotides 88–798 of SEQ ID NO: 11 and said second DNA sequence comprises nucleotides 818–1582 of SEQ ID NO:11.

26. The DNA fragment of claim 25, further comprising a third DNA sequence located between said first and second DNA sequences, said third DNA sequence consisting of nucleotides 799–817 of SEQ ID NO:11.

27. The DNA fragment of claim 24, wherein said first DNA sequence comprises the complementary sequence of nucleotides 88–798 of SEQ ID NO:11 and said second DNA sequence comprises the complementary sequence of nucleotides 818–1582 of SEQ ID NO:11.

28. The DNA fragment of claim 27, further comprising a third DNA sequence located between said first and second DNA sequences, said third DNA sequence consisting of nucleotides 799–817 of SEQ ID NO:11.

29. A recombinant expression vector for expressing, in a microorganism, an rFab against the non-neurotoxin component of botulinum complex type A or type B, said rFab having a light chain polypeptide and a heavy chain polypeptide, said expression vector comprising:

(a) a first DNA sequence which codes for said light chain polypeptide, said polypeptide having an N-terminus and a carboxyl terminus;

(b) a second DNA sequence which codes for said heavy chain polypeptide, said polypeptide having an N-terminus and a carboxyl terminus; and (c) transcriptional and translational control elements recognized by said microorganism which are operatively linked to said first and second DNA sequences; and wherein said expression vector comprises the nucleotide sequence of SEQ ID NO:1.

30. The expression vector of claim 29, further comprising a third DNA sequence coding for a histidine tail fused to the carboxyl terminus of said second DNA sequence.

31. A recombinant microorganism which expresses an rFab against the non-neurotoxin component of botulinum neurotoxin complex type A or type B, wherein the microorganism contains a recombinant expression vector which comprises the nucleotide sequence of SEQ ID NO:1.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 4435 base pairs
      (B) TYPE: nucleic acid
      (C) STRANDEDNESS: double
      (D) TOPOLOGY: circular (ii) MOLECULE TYPE: DNA (genomic)

(iii) HYPOTHETICAL: NO (iv) ANTI-SENSE: NO (vi) ORIGINAL SOURCE:
      (A) ORGANISM: Mus musculus
      (B) STRAIN: BALB/c (vii) IMMEDIATE SOURCE:
      (B) CLONE: Clone pHist 5

(xi) SEQUENCE DESCRIPTION: SEQ ID NO:1:

```
TTATATACTG ATGCACTTTT CGGGGAAATG TGCGCGGAAC CCCTATTTGT TTATTTTTCT      60

AAATACATTC AAATATGTAT CCGCTCATGA GACAATAACC CTGATAAATG CTTCAATAAT     120

ATTGAAAAAG GAAGAGTATG AGTATTCAAC ATTTCCGTGT CGCCCTTATT CCCTTTTTTG     180

CGGCATTTTG CCTTCCTGTT TTTGCTCACC CAGAAACGCT GGTGAAAGTA AAAGATGCTG     240

AAGATCAGTT GGGTGCACGA GTGGGTTACA TCGAACTGGA TCTCAACAGC GGTAAGATCC     300

TTGAGAGTTT TCGCCCCGAA GAACGTTTTC CAATGATGAG CACTTTTAAA GTTCTGCTAT     360

GTGGCGCGGT ATTATCCCGT ATTGACGCCG GGCAAGAGCA ACTCGGTCGC CGCATACACT     420

ATTCTCAGAA TGACTTGGTT GAGTACTCAC CAGTCACAGA AAAGCATCTT ACGGATGGCA     480

TGACAGTAAG AGAATTATGC AGTGCTGCCA TAACCATGAG TGATAACACT GCGGCCAACT     540

TACTTCTGAC AACGATCGGA GGACCGAAGG AGCTAACCGC TTTTTTGCAC AACATGGGGG     600

ATCATGTAAC TCGCCTTGAT CGTTGGGAAC CGGAGCTGAA TGAAGCCATA CCAAACGACG     660

AGCGTGACAC CACGATGCCT GTAGCAATGG CAACAACGTT GCGCAAACTA TTAACTGGCG     720

AACTACTTAC TCTAGCTTCC CGGCAACAAT TAATAGACTG GATGGAGGCG GATAAAGTTG     780

CAGGACCACT TCTGCGCTCG GCCCTTCCGG CTGGCTGGTT TATTGCTGAT AAATCTGGAG     840

CCGGTGAGCG TGGGTCTCGC GGTATCATTG CAGCACTGGG GCCAGATGGT AAGCCCTCCC     900

GTATCGTAGT TATCTACACG ACGGGGAGTC AGGCAACTAT GGATGAACGA AATAGACAGA     960

TCGCTGAGAT AGGTGCCTCA CTGATTAAGC ATTGGTAACT GTCAGACCAA GTTTACTCAT    1020

ATATACTTTA GATTGATTTA AAACTTCATT TTTAATTTAA AAGGATCTAG GTGAAGATCC    1080

TTTTTGATAA TCTCATGACC AAAATCCCTT AACGTGAGTT TTCGTTCCAC TGAGCGTCAG    1140

ACCCCGTAGA AAAGATCAAA GGATCTTCTT GAGATCCTTT TTTTCTGCGC GTAATCTGCT    1200

GCTTGCAAAC AAAAAAACCA CCGCTACCAG CGGTGGTTTG TTTGCCGGAT CAAGAGCTAC    1260

CAACTCTTTT TCCGAAGGTA ACTGGCTTCA GCAGAGCGCA GATACCAAAT ACTGTCCTTC    1320

TAGTGTAGCC GTAGTTAGGC CACCACTTCA AGAACTCTGT AGCACCGCCT ACATACCTCG    1380

CTCTGCTAAT CCTGTTACCA GTGGCTGCTG CCAGTGGCGA TAAGTCGTGT CTTACCGGGT    1440

TGGACTCAAG ACGATAGTTA CCGGATAAGG CGCAGCGGTC GGGCTGAACG GGGGGTTCGT    1500
```

-continued

```
GCACACAGCC CAGCTTGGAG CGAACGACCT ACACCGAACT GAGATACCTA CAGCGTGAGC    1560
TATGAGAAAG CGCCACGCTT CCCGAAGGGA GAAAGGCGGA CAGGTATCCG GTAAGCGGCA    1620
GGGTCGGAAC AGGAGAGCGC ACGAGGGAGC TTCCAGGGGG AAACGCCTGG TATCTTTATA    1680
GTCCTGTCGG GTTTCGCCAC CTCTGACTTG AGCGTCGATT TTTGTGATGC TCGTCAGGGG    1740
GGCGGAGCCT ATGGAAAAAC GCCAGCAACG CGGCCTTTTT ACGGTTCCTG GCCTTTTGCT    1800
GGCCTTTTGC TCACATGTTC TTTCCTGCGT TATCCCCTGA TTCTGTGGAT AACCGTATTA    1860
CCGCCTTTGA GTGAGCTGAT ACCGCTCGCC GCAGCCGAAC GACCGAGCGC AGCGAGTCAG    1920
TGAGCGAGGA AGCGGAAGAG CGCCCAATAC GCAAACCGCC TCTCCCCGCG CGTTGGCCGA    1980
TTCATTAATG CAGCTGGCAC GACAGGTTTC CCGACTGGAA AGCGGGCAGT GAGCGCAACG    2040
CAATTAATGT GAGTTAGCTC ACTCATTAGG CACCCCAGGC TTTACACTTT ATGCTTCCGG    2100
CTCGTATGTT GTGTGGAATT GTGAGCGGAT AACAATTTCA CACAGGAAAC AGCTATGACC    2160
ATGATTACGC CAAGCTCGAA ATTAACCCTC ACTAAAGGGA ACAAAAGCTG GAGCTTGAAT    2220
TCTTAACTAC TCGCCAAGGA GACAGTCATA ATGAAATACC TATTGCCTAC GGCGGCCGCT    2280
GGATTGTTAT TACTCGCTGC CCAACCAGCC ATGGCCGACA TCCAGATGAC CCAGTCTCCA    2340
GCCTCCCTAT CTGCATCTGT GGGAGAAACT GTCACTATCA CATGTCGAGC AAGTGGGAAT    2400
ATTCACAATT ATTTAGCATG GTATCAGCAG AAACAGGGAA AATCTCCTCA GCTCCTGGTC    2460
TATAATGCAA AAACCTTAGC AGATGGTGTG CCATCAAGGT TCAGTGGCAG TGGATCAGGA    2520
ACACAATATT CTCTCAAGAT CAACAGCCTG CAGCCTGAAG ATTTTGGGAG TTATTACTGT    2580
CAACATTTTT GGAGTACTCC GTGGACGTTC GGTGGAGGCA CCAAGCTGGA AATCAAACGG    2640
GCTGATGCTG CACCAACTGT ATCCATCTTC CCACCATCCA GTGAGCAGTT AACATCTGGA    2700
GGTGCCTCAG TCGTGTGCTT CTTGAACAAC TTCTACCCCA AAGACATCAA TGTCAAGTGG    2760
AAGATTGATG GCAGTGAACG ACAAAATGGC GTCCTGAACA GTTGGACTGA TCAGGACAGC    2820
AAAGACAGCA CCTACAGCAT GAGCAGCACC CTCACATTGA CCAAGGACGA GTATGAACGA    2880
CATAACAGCT ATACCTGTGA GGCCACTCAC AAGACATCAA CTTCACCCAT TGTCAAGAGC    2940
TTCAACAGGA ATGAGTGTTA ATAGCAAGGA GACAGTCATA ATGAAATACC TATTGCCTAC    3000
GGCAGCCGCT GGATTGTTAT TACTCGCGGC CCAACCGGCC ATGGCCGAGG TTCAGCTTCA    3060
GCAGTCTGGG GCAGAGCTTG TGAAGCCAGG GGCCTCAGTC AAGTTGTCCT GCACAGCTTC    3120
TGGCTTCAAC ATTAAAGACA CCTTTATGCA CTGGGTGAAG CAGAGGCCTG AACAGGGCCT    3180
GGAGTGGATT GGAAGGATTG ATCCTGCGAA TGGGAATACT GAATATGACC CGAAGTTCCA    3240
GGGCAAGGCC ACTATAACAG CAGACACATC CTCCAACACA GTCAACCTGC AGCTCAGCAG    3300
CCTGACATCT GAGGACACTG CCGTCTATTA CTGTGCTAGT GGAGGGGAAC TGGGGTTTCC    3360
TTACTGGGGC CAAGGGACTC TGGTCACTGT CTCTGCAGCC AAAACGACAC CCCCATCTGT    3420
CTATCCACTG GCCCCTGGAT CTGCTGCCCA AACTAACTCC ATGGTGACCC TGGGATGCCT    3480
GGTCAAGGGC TATTTCCCTG AGCCAGTGAC AGTGACCTGG AACTCTGGAT CCCTGTCCAG    3540
CGGTGTGCAC ACCTTCCCAG CTGTCCTGCA GTTTGACCTC TACACTCTGA GCAGCTCAGT    3600
GACTGTCCCC TCCAGCACCT GGCCCAGCGA GACCGTCACC TGCAACGTTG CCCACCCGGC    3660
CAGCAGCACC AAGGTGGACA AGAAAATTGT GCCCAGGGAT TGTACTAGTG AGGTGGAGG    3720
TAGCCACCAT CACCATCACC ATTAATCTAG AGTTAAGCGG CCGTCGAGGG GGGCCCGGT    3780
ACCCAATTCG CCCTATAGTG AGTCGTATTA CAATTCACTG GCCGTCGTTT TACAACGTCG    3840
TGACTGGGAA AACCCTGGCG TTACCCAACT TAATCGCCTT GCAGCACATC CCCCTTTCGC    3900
```

```
CAGCTGGCGT AATAGCGAAG AGGCCCGCAC CGATCGCCCT TCCCAACAGT TGCGCAGCCT      3960

GAATGGCGAA TGGAAATTGT AAGCGTTAAT ATTTTGTTAA AATTCGCGTT AAATTTTTGT      4020

TAAATCAGCT CATTTTTTAA CCAATAGGCC GAAATCGGCA AAATCCCTTA TAAATCAAAA      4080

GAATAGACCG AGATAGGGTT GAGTGTTGTT CCAGTTTGGA ACAAGAGTCC ACTATTAAAG      4140

AACGTGGACT CCAACGTCAA AGGGCGAAAA ACCGTCTATC AGGGCGATGG CCCACTACGT      4200

GAACCATCAC CCTAATCAAG TTTTTTGGGG TCGAGGTGCC GTAAAGCACT AAATCGGAAC      4260

CCTAAAGGGA GCCCCCGATT TAGAGCTTGA CGGGGAAAGC CGGCGAACGT GGCGAGAAAG      4320

GAAGGGAAGA AAGCGAAAGG AGCGGGCGCT AGGGCGCTGG CAAGTGTAGC GGTCACGCTG      4380

CGCGTAACCA CCACACCCGC CGCGCTTAAT GCGCCGCTAC AGGGCGCGTC AGGTG          4435
```

(2) INFORMATION FOR SEQ ID NO:2:

(i) SEQUENCE CHARACTERISTICS:
        (A) LENGTH: 1672 base pairs
        (B) TYPE: nucleic acid
        (C) STRANDEDNESS: double
        (D) TOPOLOGY: Not Relevant (ii) MOLECULE TYPE: cDNA (iii) HYPOTHETICAL: NO (iv) ANTI-SENSE: NO (vi) ORIGINAL SOURCE:
        (A) ORGANISM: Mus musculus
        (B) STRAIN: Balb/c (vii) IMMEDIATE SOURCE:
        (B) CLONE: pHist 5

(ix) FEATURE:
        (A) NAME/KEY: CDS
        (B) LOCATION: 117..827
        (D) OTHER INFORMATION: /product= "antibody fragment, light
            chain"
            /label= BotFab 5

(ix) FEATURE:
        (A) NAME/KEY: CDS
        (B) LOCATION: 847..1611
        (D) OTHER INFORMATION: /product= "antibody fragment, heavy
            chain"
            /label= BotFab 5

(xi) SEQUENCE DESCRIPTION: SEQ ID NO:2:

```
TAGTTATCTC CTTATGTTTC TATTCTCTTT CTCTTACCCA AGCTCGAATT AACCTCACTA       60

AAGGGAACAA AAGCTGGAGC TTGAATTCTT AACTACTCGC CAAGGAGACA GTCATA         116

ATG AAA TAC CTA TTG CCT ACG GCG GCC GCT GGA TTG TTA TTA CTC GCT       164
Met Lys Tyr Leu Leu Pro Thr Ala Ala Ala Gly Leu Leu Leu Leu Ala
 1               5                  10                  15

GCC CAA CCA GCC ATG GCC GAC ATC CAG ATG ACC CAG TCT CCA GCC TCC       212
Ala Gln Pro Ala Met Ala Asp Ile Gln Met Thr Gln Ser Pro Ala Ser
                 20                  25                  30

CTA TCT GCA TCT GTG GGA GAA ACT GTC ACT ATC ACA TGT CGA GCA AGT       260
Leu Ser Ala Ser Val Gly Glu Thr Val Thr Ile Thr Cys Arg Ala Ser
             35                  40                  45

GGG AAT ATT CAC AAT TAT TTA GCA TGG TAT CAG CAG AAA CAG GGA AAA       308
Gly Asn Ile His Asn Tyr Leu Ala Trp Tyr Gln Gln Lys Gln Gly Lys
         50                  55                  60

TCT CCT CAG CTC CTG GTC TAT AAT GCA AAA ACC TTA GCA GAT GGT GTG       356
Ser Pro Gln Leu Leu Val Tyr Asn Ala Lys Thr Leu Ala Asp Gly Val
 65                  70                  75                  80
```

```
CCA TCA AGG TTC AGT GGC AGT GGA TCA GGA ACA CAA TAT TCT CTC AAG        404
Pro Ser Arg Phe Ser Gly Ser Gly Ser Gly Thr Gln Tyr Ser Leu Lys
                 85                  90                  95

ATC AAC AGC CTG CAG CCT GAA GAT TTT GGG AGT TAT TAC TGT CAA CAT        452
Ile Asn Ser Leu Gln Pro Glu Asp Phe Gly Ser Tyr Tyr Cys Gln His
                100                 105                 110

TTT TGG AGT ACT CCG TGG ACG TTC GGT GGA GGC ACC AAG CTG GAA ATC        500
Phe Trp Ser Thr Pro Trp Thr Phe Gly Gly Gly Thr Lys Leu Glu Ile
            115                 120                 125

AAA CGG GCT GAT GCT GCA CCA ACT GTA TCC ATC TTC CCA CCA TCC AGT        548
Lys Arg Ala Asp Ala Ala Pro Thr Val Ser Ile Phe Pro Pro Ser Ser
        130                 135                 140

GAG CAG TTA ACA TCT GGA GGT GCC TCA GTC GTG TGC TTC TTG AAC AAC        596
Glu Gln Leu Thr Ser Gly Gly Ala Ser Val Val Cys Phe Leu Asn Asn
145                 150                 155                 160

TTC TAC CCC AAA GAC ATC AAT GTC AAG TGG AAG ATT GAT GGC AGT GAA        644
Phe Tyr Pro Lys Asp Ile Asn Val Lys Trp Lys Ile Asp Gly Ser Glu
                165                 170                 175

CGA CAA AAT GGC GTC CTG AAC AGT TGG ACT GAT CAG GAC AGC AAA GAC        692
Arg Gln Asn Gly Val Leu Asn Ser Trp Thr Asp Gln Asp Ser Lys Asp
            180                 185                 190

AGC ACC TAC AGC ATG AGC AGC ACC CTC ACA TTG ACC AAG GAC GAG TAT        740
Ser Thr Tyr Ser Met Ser Ser Thr Leu Thr Leu Thr Lys Asp Glu Tyr
        195                 200                 205

GAA CGA CAT AAC AGC TAT ACC TGT GAG GCC ACT CAC AAG ACA TCA ACT        788
Glu Arg His Asn Ser Tyr Thr Cys Glu Ala Thr His Lys Thr Ser Thr
210                 215                 220

TCA CCC ATT GTC AAG AGC TTC AAC AGG AAT GAG TGT TAA TAGCAAGGAG        837
Ser Pro Ile Val Lys Ser Phe Asn Arg Asn Glu Cys
225                 230                 235

ACAGTCATA ATG AAA TAC CTA TTG CCT ACG GCA GCC GCT GGA TTG TTA         885
          Met Lys Tyr Leu Leu Pro Thr Ala Ala Ala Gly Leu Leu
            1               5                  10

TTA CTC GCG GCC CAA CCG GCC ATG GCC GAG GTT CAG CTT CAG CAG TCT        933
Leu Leu Ala Ala Gln Pro Ala Met Ala Glu Val Gln Leu Gln Gln Ser
        15                  20                  25

GGG GCA GAG CTT GTG AAG CCA GGG GCC TCA GTC AAG TTG TCC TGC ACA        981
Gly Ala Glu Leu Val Lys Pro Gly Ala Ser Val Lys Leu Ser Cys Thr
30                  35                  40                  45

GCT TCT GGC TTC AAC ATT AAA GAC ACC TTT ATG CAC TGG GTG AAG CAG        1029
Ala Ser Gly Phe Asn Ile Lys Asp Thr Phe Met His Trp Val Lys Gln
                50                  55                  60

AGG CCT GAA CAG GGC CTG GAG TGG ATT GGA AGG ATT GAT CCT GCG AAT        1077
Arg Pro Glu Gln Gly Leu Glu Trp Ile Gly Arg Ile Asp Pro Ala Asn
            65                  70                  75

GGG AAT ACT GAA TAT GAC CCG AAG TTC CAG GGC AAG GCC ACT ATA ACA        1125
Gly Asn Thr Glu Tyr Asp Pro Lys Phe Gln Gly Lys Ala Thr Ile Thr
        80                  85                  90

GCA GAC ACA TCC TCC AAC ACA GTC AAC CTG CAG CTC AGC AGC CTG ACA        1173
Ala Asp Thr Ser Ser Asn Thr Val Asn Leu Gln Leu Ser Ser Leu Thr
    95                  100                 105

TCT GAG GAC ACT GCC GTC TAT TAC TGT GCT AGT GGA GGG GAA CTG GGG        1221
Ser Glu Asp Thr Ala Val Tyr Tyr Cys Ala Ser Gly Gly Glu Leu Gly
110                 115                 120                 125

TTT CCT TAC TGG GGC CAA GGG ACT CTG GTC ACT GTC TCT GCA GCC AAA        1269
Phe Pro Tyr Trp Gly Gln Gly Thr Leu Val Thr Val Ser Ala Ala Lys
                130                 135                 140

ACG ACA CCC CCA TCT GTC TAT CCA CTG GCC CCT GGA TCT GCT GCC CAA        1317
Thr Thr Pro Pro Ser Val Tyr Pro Leu Ala Pro Gly Ser Ala Ala Gln
            145                 150                 155
```

```
ACT AAC TCC ATG GTG ACC CTG GGA TGC CTG GTC AAG GGC TAT TTC CCT    1365
Thr Asn Ser Met Val Thr Leu Gly Cys Leu Val Lys Gly Tyr Phe Pro
        160                 165                 170

GAG CCA GTG ACA GTG ACC TGG AAC TCT GGA TCC CTG TCC AGC GGT GTG    1413
Glu Pro Val Thr Val Thr Trp Asn Ser Gly Ser Leu Ser Ser Gly Val
175                 180                 185

CAC ACC TTC CCA GCT GTC CTG CAG TTT GAC CTC TAC ACT CTG AGC AGC    1461
His Thr Phe Pro Ala Val Leu Gln Phe Asp Leu Tyr Thr Leu Ser Ser
190                 195                 200                 205

TCA GTG ACT GTC CCC TCC AGC ACC TGG CCC AGC GAG ACC GTC ACC TGC    1509
Ser Val Thr Val Pro Ser Ser Thr Trp Pro Ser Glu Thr Val Thr Cys
        210                 215                 220

AAC GTT GCC CAC CCG GCC AGC AGC ACC AAG GTG GAC AAG AAA ATT GTG    1557
Asn Val Ala His Pro Ala Ser Ser Thr Lys Val Asp Lys Lys Ile Val
            225                 230                 235

CCC AGG GAT TGT ACT AGT GGA GGT GGA GGT AGC CAC CAT CAC CAT CAC    1605
Pro Arg Asp Cys Thr Ser Gly Gly Gly Gly Ser His His His His His
                240                 245                 250

CAT TAA TCTAGAGTTA AGCGGCCGTC GAGGGGGGGC CCGGTACCCA ATTCGCCCTA    1661
His

TAGTGAGTCG T                                                      1672

(2) INFORMATION FOR SEQ ID NO:3:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:3:

Met Lys Tyr Leu Leu Pro Thr Ala Ala Ala Gly Leu Leu Leu Leu Ala
1               5                   10                  15

Ala Gln Pro Ala Met Ala Asp Ile Gln Met Thr Gln Ser Pro Ala Ser
                20                  25                  30

Leu Ser Ala Ser Val Gly Glu Thr Val Thr Ile Thr Cys Arg Ala Ser
            35                  40                  45

Gly Asn Ile His Asn Tyr Leu Ala Trp Tyr Gln Gln Lys Gln Gly Lys
        50                  55                  60

Ser Pro Gln Leu Leu Val Tyr Asn Ala Lys Thr Leu Ala Asp Gly Val
65                  70                  75                  80

Pro Ser Arg Phe Ser Gly Ser Gly Ser Gly Thr Gln Tyr Ser Leu Lys
                85                  90                  95

Ile Asn Ser Leu Gln Pro Glu Asp Phe Gly Ser Tyr Tyr Cys Gln His
                100                 105                 110

Phe Trp Ser Thr Pro Trp Thr Phe Gly Gly Gly Thr Lys Leu Glu Ile
            115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
                180                 185                 190

Ser Thr Tyr Ser Met Ser Ser Thr Leu Thr Leu Thr Lys Asp Glu Tyr
            195                 200                 205
```

```
Glu Arg His Asn Ser Tyr Thr Cys Glu Ala Thr His Lys Thr Ser Thr
        210                 215                 220

Ser Pro Ile Val Lys Ser Phe Asn Arg Asn Glu Cys
225                 230                 235
```

(2) INFORMATION FOR SEQ ID NO:4:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Tyr Leu Leu Pro Thr Ala Ala Ala Gly Leu Leu Leu Leu Ala
 1               5                  10                  15

Ala Gln Pro Ala Met Ala Glu Val Gln Leu Gln Gln Ser Gly Ala Glu
                20                  25                  30

Leu Val Lys Pro Gly Ala Ser Val Lys Leu Ser Cys Thr Ala Ser Gly
                35                  40                  45

Phe Asn Ile Lys Asp Thr Phe Met His Trp Val Lys Gln Arg Pro Glu
 50                  55                  60

Gln Gly Leu Glu Trp Ile Gly Arg Ile Asp Pro Ala Asn Gly Asn Thr
 65                  70                  75                  80

Glu Tyr Asp Pro Lys Phe Gln Gly Lys Ala Thr Ile Thr Ala Asp Thr
                85                  90                  95

Ser Ser Asn Thr Val Asn Leu Gln Leu Ser Ser Leu Thr Ser Glu Asp
                100                 105                 110

Thr Ala Val Tyr Tyr Cys Ala Ser Gly Gly Glu Leu Gly Phe Pro Tyr
                115                 120                 125

Trp Gly Gln Gly Thr Leu Val Thr Val Ser Ala Ala Lys Thr Thr Pro
                130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
                180                 185                 190

Pro Ala Val Leu Gln Phe Asp Leu Tyr Thr Leu Ser Ser Ser Val Thr
                195                 200                 205

Val Pro Ser Ser Thr Trp Pro Ser Glu Thr Val Thr Cys Asn Val Ala
210                 215                 220

His Pro Ala Ser Ser Thr Lys Val Asp Lys Lys Ile Val Pro Arg Asp
225                 230                 235                 240

Cys Thr Ser Gly Gly Gly Gly Ser His His His His His
                245                 250
```

(2) INFORMATION FOR SEQ ID NO:5:

(i) SEQUENCE CHARACTERISTICS:
        (A) LENGTH: 1641 base pairs
        (B) TYPE: nucleic acid
        (C) STRANDEDNESS: double
        (D) TOPOLOGY: Not Relevant (ii) MOLECULE TYPE: cDNA (iii) HYPOTHETICAL: NO -continued

```
    (iv) ANTI-SENSE: NO (vi) ORIGINAL SOURCE:
          (A) ORGANISM: Mus musculus
          (B) STRAIN: BALB/c (vii) IMMEDIATE SOURCE:
          (B) CLONE: pHist 1

(ix) FEATURE:
          (A) NAME/KEY: CDS
          (B) LOCATION: 87..788
          (D) OTHER INFORMATION: /product= "antibody fragment, light
                chain"
                /label= BotFab 1

(ix) FEATURE:
          (A) NAME/KEY: CDS
          (B) LOCATION: 815..1579
          (D) OTHER INFORMATION: /product= "antibody fragment, Heavy
                Chain"
                /label= BotFab 1

(xi) SEQUENCE DESCRIPTION: SEQ ID NO:5:

ATACGCCAAG CTCGAAATTA ACCCTCACTA AAGGGAACAA AAGCTGGAGC TTGAATTCTT      60

AACTACTCGC CAAGGAGACA GTCATA ATG AAA TAC CTA TTG CCT ACG GCG GCC      113
                             Met Lys Tyr Leu Leu Pro Thr Ala Ala
                               1               5

GCT GGA TTG TTA TTA CTC GCT GCC CAA CCA GCC ATG GCC GAC ATC CAG      161
Ala Gly Leu Leu Leu Leu Ala Ala Gln Pro Ala Met Ala Asp Ile Gln
 10                  15                  20                  25

ATG ACC CAG TCT CCA GCC TCC CTA TCT GCA TCT GTG GGA GAA ACT GTC      209
Met Thr Gln Ser Pro Ala Ser Leu Ser Ala Ser Val Gly Glu Thr Val
                 30                  35                  40

ACT ATC ACA TGT CGA GCA AGT GGG AAT ATT CAC AAT TAT TTA GCA TGG      257
Thr Ile Thr Cys Arg Ala Ser Gly Asn Ile His Asn Tyr Leu Ala Trp
             45                  50                  55

TAT CAG CAG AAA CAG GGA AAA TCT CCT CAG CTC CTG GTC TAT AAT GCA      305
Tyr Gln Gln Lys Gln Gly Lys Ser Pro Gln Leu Leu Val Tyr Asn Ala
         60                  65                  70

AAA ACC TTA GCA GAT GGT GTG CCA TCA AGG TTC AGT GGC AGT GGA TCA      353
Lys Thr Leu Ala Asp Gly Val Pro Ser Arg Phe Ser Gly Ser Gly Ser
     75                  80                  85

GGA ACA CAA TAT TCT CTC AAG ATC AAC AGC CTG CAG CCT GAA GAT TTT      401
Gly Thr Gln Tyr Ser Leu Lys Ile Asn Ser Leu Gln Pro Glu Asp Phe
 90                  95                 100                 105

GGG AGT TAT TAC TGT CAA CAT TTT TGG AGT ACT CCG TGG ACG TTC GGT      449
Gly Ser Tyr Tyr Cys Gln His Phe Trp Ser Thr Pro Trp Thr Phe Gly
                110                 115                 120

GGA GGC ACC AAG CTG GAA ATC AAA CGG GCT GAT GCT GCA CCA ACT GTA      497
Gly Gly Thr Lys Leu Glu Ile Lys Arg Ala Asp Ala Ala Pro Thr Val
            125                 130                 135

TCC ATC TTC CCA CCA TCC AGT GAG CAG TTA ACA TCT GGA GGT GCC TCA      545
Ser Ile Phe Pro Pro Ser Ser Glu Gln Leu Thr Ser Gly Gly Ala Ser
        140                 145                 150

GTC GTG TGC TTC TTG AAC AAC TTC TAC CCC AAA GAC ATC AAT GTC AAG      593
Val Val Cys Phe Leu Asn Asn Phe Tyr Pro Lys Asp Ile Asn Val Lys
    155                 160                 165

TGG AAG ATT GAT GGC AGT GAA CGA CAA AAT GGC GTC CTG AAC AGT TGG      641
Trp Lys Ile Asp Gly Ser Glu Arg Gln Asn Gly Val Leu Asn Ser Trp
170                 175                 180                 185

ACT GAT CAG GAC AGC AAA GAC AGC ACC TAC AGC ATG AGC AGC ACC CTC      689
Thr Asp Gln Asp Ser Lys Asp Ser Thr Tyr Ser Met Ser Ser Thr Leu
                190                 195                 200
```

```
ACA TTG ACC AAG GAC GAG TAT GAA CGA CAT AAC AGC TAT ACC TGT GAG        737
Thr Leu Thr Lys Asp Glu Tyr Glu Arg His Asn Ser Tyr Thr Cys Glu
            205                 210                 215

GCC ACT CAC AAG ACA TCA ACT TCC CCA TTG TCT AGA GCT TCC CAG GAA        785
Ala Thr His Lys Thr Ser Thr Ser Pro Leu Ser Arg Ala Ser Gln Glu
            220                 225                 230

TGA GTGTTTATAG CAAGGAAACA GTCATA ATG AAA TAC CTA TTG CCT ACG GCA       838
                                  Met Lys Tyr Leu Leu Pro Thr Ala
                                   1               5

GCC GCT GGA TTG TTA TTA CTC GCG GCC CAA CCG GCG ATG GCC GAG GTT        886
Ala Ala Gly Leu Leu Leu Leu Ala Ala Gln Pro Ala Met Ala Glu Val
         10              15              20

CAG CTT CAG CAG TCT GGG GCA GAG CTT GTG AAG CCA GGG GCC TCA GTC        934
Gln Leu Gln Gln Ser Gly Ala Glu Leu Val Lys Pro Gly Ala Ser Val
 25              30              35                          40

AAG TTG TCC TGC ACA GCT TCT GGC TTC AAC ATT AAA GAC ACC TTT ATG        982
Lys Leu Ser Cys Thr Ala Ser Gly Phe Asn Ile Lys Asp Thr Phe Met
                 45              50              55

CAC TGG GTG AAG CAG AGG CCT GAA CAG GGC CTG GAG TGG ATT GGA AGG       1030
His Trp Val Lys Gln Arg Pro Glu Gln Gly Leu Glu Trp Ile Gly Arg
             60              65              70

ATT GAT CCT GCG AAT GGG AAT ACT GAA TAT GAC CCG AAG TTC CAG GGC       1078
Ile Asp Pro Ala Asn Gly Asn Thr Glu Tyr Asp Pro Lys Phe Gln Gly
         75              80              85

AAG GCC ACT ATA ACA GCA GAC ACA TCC TCC AAC ACA GTC AAC CTG CAG       1126
Lys Ala Thr Ile Thr Ala Asp Thr Ser Ser Asn Thr Val Asn Leu Gln
 90              95              100

CTC AGC AGC CTG ACA TCT GAG GAC ACT GCC GTC TAT TAC TGT GCT AGT       1174
Leu Ser Ser Leu Thr Ser Glu Asp Thr Ala Val Tyr Tyr Cys Ala Ser
105             110             115                         120

GGA GGG GAA CTG GGG TTT CCT TAC TGG GGC CAA GGG ACT CTG GTC ACT       1222
Gly Gly Glu Leu Gly Phe Pro Tyr Trp Gly Gln Gly Thr Leu Val Thr
            125             130             135

GTC TCT GCA GCC AAA ACG ACA CCC CCA TCT GTC TAT CCA CTG GCC CCT       1270
Val Ser Ala Ala Lys Thr Thr Pro Pro Ser Val Tyr Pro Leu Ala Pro
            140             145             150

GGA TCT GCT GCC CAA ACT AAC TCC ATG GTG ACC CTG GGA TGC CTG GTC       1318
Gly Ser Ala Ala Gln Thr Asn Ser Met Val Thr Leu Gly Cys Leu Val
            155             160             165

AAG GGC TAT TTC CCT GAG CCA GTG ACA GTG ACC TGG AAC TCT GGA TCC       1366
Lys Gly Tyr Phe Pro Glu Pro Val Thr Val Thr Trp Asn Ser Gly Ser
    170             175             180

CTG TCC AGC GGT GTG CAC ACC TTC CCA GCT GTC CTG CAG TAT GAC CTC       1414
Leu Ser Ser Gly Val His Thr Phe Pro Ala Val Leu Gln Tyr Asp Leu
185             190             195                         200

TAC ACT CTG AGC AGC TCA GTG ACT GTC CCC TCC AGC ACC TGG CCC AGC       1462
Tyr Thr Leu Ser Ser Ser Val Thr Val Pro Ser Ser Thr Trp Pro Ser
            205             210             215

GAG ACC GTC ACC TGC AAC GTT GCC CAC CCG GCC AGC AGC ACC AAG GTG       1510
Glu Thr Val Thr Cys Asn Val Ala His Pro Ala Ser Ser Thr Lys Val
            220             225             230

GAC AAG AAA ATT GTG CCC AGG GAT TGT ACT AGT GGA GGT GGA GGT AGC       1558
Asp Lys Lys Ile Val Pro Arg Asp Cys Thr Ser Gly Gly Gly Gly Ser
        235             240             245

CAC CAT CAC CAT CAC CAT TAA TCTAGAGTTA AGCGGCCGTC GAGGGGGGGC          1609
His His His His His His
        250

CCGGTACCCA ATTCGCCCTA TAGTGAGTCG TA                                   1641
```

(2) INFORMATION FOR SEQ ID NO:6:

(i) SEQUENCE CHARACTERISTICS:
    (A) LENGTH: 233 amino acids
    (B) TYPE: amino acid
    (D) TOPOLOGY: linear (ii) MOLECULE TYPE: protein (xi) SEQUENCE DESCRIPTION: SEQ ID NO:6:

Met Lys Tyr Leu Leu Pro Thr Ala Ala Ala Gly Leu Leu Leu Leu Ala
 1               5                  10                  15

Ala Gln Pro Ala Met Ala Asp Ile Gln Met Thr Gln Ser Pro Ala Ser
            20                  25                  30

Leu Ser Ala Ser Val Gly Glu Thr Val Thr Ile Thr Cys Arg Ala Ser
        35                  40                  45

Gly Asn Ile His Asn Tyr Leu Ala Trp Tyr Gln Gln Lys Gln Gly Lys
    50                  55                  60

Ser Pro Gln Leu Leu Val Tyr Asn Ala Lys Thr Leu Ala Asp Gly Val
65                  70                  75                  80

Pro Ser Arg Phe Ser Gly Ser Gly Ser Gly Thr Gln Tyr Ser Leu Lys
                85                  90                  95

Ile Asn Ser Leu Gln Pro Glu Asp Phe Gly Ser Tyr Tyr Cys Gln His
            100                 105                 110

Phe Trp Ser Thr Pro Trp Thr Phe Gly Gly Gly Thr Lys Leu Glu Ile
        115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
210                 215                 220

Ser Pro Leu Ser Arg Ala Ser Gln Glu
225                 230

(2) INFORMATION FOR SEQ ID NO:7:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO:7:

Met Lys Tyr Leu Leu Pro Thr Ala Ala Ala Gly Leu Leu Leu Leu Ala
 1               5                  10                  15

Ala Gln Pro Ala Met Ala Glu Val Gln Leu Gln Gln Ser Gly Ala Glu
            20                  25                  30

Leu Val Lys Pro Gly Ala Ser Val Lys Leu Ser Cys Thr Ala Ser Gly
        35                  40                  45

Phe Asn Ile Lys Asp Thr Phe Met His Trp Val Lys Gln Arg Pro Glu
    50                  55                  60

```
Gln Gly Leu Glu Trp Ile Gly Arg Ile Asp Pro Ala Asn Gly Asn Thr
 65              70                  75                  80

Glu Tyr Asp Pro Lys Phe Gln Gly Lys Ala Thr Ile Thr Ala Asp Thr
                 85                  90                  95

Ser Ser Asn Thr Val Asn Leu Gln Leu Ser Ser Leu Thr Ser Glu Asp
            100                 105                 110

Thr Ala Val Tyr Tyr Cys Ala Ser Gly Gly Glu Leu Gly Phe Pro Tyr
        115                 120                 125

Trp Gly Gln Gly Thr Leu Val Thr Val Ser Ala Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
                180                 185                 190

Pro Ala Val Leu Gln Tyr Asp Leu Tyr Thr Leu Ser Ser Ser Val Thr
            195                 200                 205

Val Pro Ser Ser Thr Trp Pro Ser Glu Thr Val Thr Cys Asn Val Ala
210                 215                 220

His Pro Ala Ser Ser Thr Lys Val Asp Lys Lys Ile Val Pro Arg Asp
225                 230                 235                 240

Cys Thr Ser Gly Gly Gly Gly Ser His His His His His
                245                 250
```

(2) INFORMATION FOR SEQ ID NO:8:

(i) SEQUENCE CHARACTERISTICS:
        (A) LENGTH: 1632 base pairs
        (B) TYPE: nucleic acid
        (C) STRANDEDNESS: double
        (D) TOPOLOGY: Not Relevant (ii) MOLECULE TYPE: cDNA (iii) HYPOTHETICAL: NO (iv) ANTI-SENSE: NO (vi) ORIGINAL SOURCE:
        (A) ORGANISM: Mus musculus
        (B) STRAIN: BALB/c (vii) IMMEDIATE SOURCE:
        (B) CLONE: pHist 20

(ix) FEATURE:
        (A) NAME/KEY: CDS
        (B) LOCATION: 88..798
        (D) OTHER INFORMATION: /product= "antibody fragment, light
           chain"
           /label= BotFab 20

(ix) FEATURE:
        (A) NAME/KEY: CDS
        (B) LOCATION: 818..1582
        (D) OTHER INFORMATION: /product= "antibody fragment, Heavy
           Chain"
           /label= BotFab 20

(xi) SEQUENCE DESCRIPTION: SEQ ID NO:8:

```
TATACGCCAA GCTCGAAATT AACCCTCACT AAAGGGAACA AAAGCTGGAG CTTGAATTCT      60

TAACTACTCG CCAAGGAGAC AGTCATA ATG AAA TAC CTA TTG CCT ACG GCG         111
                              Met Lys Tyr Leu Leu Pro Thr Ala
                                1               5
```

| | | | | | | | | | | | | | | | |
|---|---|---|---|---|---|---|---|---|---|---|---|---|---|---|---|
| GCC | GCT | GGA | TTG | TTA | TTA | CTC | GCT | GCC | CAA | CCA | GCC | ATG | GCC | GAC | ATC | 159 |
| Ala | Ala | Gly | Leu | Leu | Leu | Leu | Ala | Ala | Gln | Pro | Ala | Met | Ala | Asp | Ile |
| | 10 | | | | 15 | | | | | 20 | | | | | |

| CAG | ATG | ACC | CAG | TCT | CCA | GCC | TCC | CTA | TCT | GCA | TCT | GTG | GGA | GAA | ACT | 207 |
| Gln | Met | Thr | Gln | Ser | Pro | Ala | Ser | Leu | Ser | Ala | Ser | Val | Gly | Glu | Thr |
| 25 | | | | | 30 | | | | | 35 | | | | | 40 |

| GTC | ACT | ATC | ACA | TGT | CGA | GCA | AGT | GGG | AAT | ATT | CAC | AAT | TAT | TTA | GCA | 255 |
| Val | Thr | Ile | Thr | Cys | Arg | Ala | Ser | Gly | Asn | Ile | His | Asn | Tyr | Leu | Ala |
| | | | | 45 | | | | | 50 | | | | | 55 | |

| TGG | TAT | CAG | CAG | AAA | CAG | GGG | AAA | TCT | CCT | CAG | CTC | CTG | GTC | TAT | AAT | 303 |
| Trp | Tyr | Gln | Gln | Lys | Gln | Gly | Lys | Ser | Pro | Gln | Leu | Leu | Val | Tyr | Asn |
| | | | 60 | | | | | 65 | | | | | 70 | | |

| GCA | AAA | ACC | TTA | GCA | GAT | GGT | GTG | CCA | TCA | AGG | TTC | AGT | GGC | AGT | GGA | 351 |
| Ala | Lys | Thr | Leu | Ala | Asp | Gly | Val | Pro | Ser | Arg | Phe | Ser | Gly | Ser | Gly |
| | | 75 | | | | | 80 | | | | | 85 | | | |

| TCA | GGA | ACA | CAA | TAT | TCT | CTC | AAG | ATC | AAC | AGC | CTG | CAG | CCT | GAA | GAT | 399 |
| Ser | Gly | Thr | Gln | Tyr | Ser | Leu | Lys | Ile | Asn | Ser | Leu | Gln | Pro | Glu | Asp |
| | 90 | | | | | 95 | | | | | 100 | | | | |

| TTT | GGG | AGT | TAT | TAC | TGT | CAA | CAT | TTT | TGG | AGT | ACT | CCG | TGG | ACG | TTC | 447 |
| Phe | Gly | Ser | Tyr | Tyr | Cys | Gln | His | Phe | Trp | Ser | Thr | Pro | Trp | Thr | Phe |
| 105 | | | | 110 | | | | | 115 | | | | | 120 | |

| GGT | GGA | GGC | ACC | AAG | CTG | GAA | ATC | AAA | CGG | GCT | GAT | GCT | GCA | CCA | ACT | 495 |
| Gly | Gly | Gly | Thr | Lys | Leu | Glu | Ile | Lys | Arg | Ala | Asp | Ala | Ala | Pro | Thr |
| | | | 125 | | | | | 130 | | | | | 135 | | |

| GTA | TCC | ATC | TTC | CCA | CCA | TCC | AGT | GAG | CAG | TTA | ACA | TCT | GGA | GGT | GCC | 543 |
| Val | Ser | Ile | Phe | Pro | Pro | Ser | Ser | Glu | Gln | Leu | Thr | Ser | Gly | Gly | Ala |
| | | | 140 | | | | | 145 | | | | | 150 | | |

| TCA | GTC | GTG | TGC | TTC | TTG | AAC | AAC | TTC | TAC | CCC | AAA | GAC | ATC | AAT | GTC | 591 |
| Ser | Val | Val | Cys | Phe | Leu | Asn | Asn | Phe | Tyr | Pro | Lys | Asp | Ile | Asn | Val |
| | | 155 | | | | | 160 | | | | | 165 | | | |

| AAG | TGG | AAG | ATT | GAT | GGC | AGT | GAA | CGA | CAA | AAT | GGC | GTC | CTG | AAC | AGT | 639 |
| Lys | Trp | Lys | Ile | Asp | Gly | Ser | Glu | Arg | Gln | Asn | Gly | Val | Leu | Asn | Ser |
| 170 | | | | | 175 | | | | | 180 | | | | | |

| TGG | ACT | GAT | CAG | GAC | AGC | AAA | GAC | AGC | ACC | TAC | AGC | ATG | AGC | AGC | ACC | 687 |
| Trp | Thr | Asp | Gln | Asp | Ser | Lys | Asp | Ser | Thr | Tyr | Ser | Met | Ser | Ser | Thr |
| 185 | | | | 190 | | | | | 195 | | | | | 200 | |

| CTC | ACA | TTG | ACC | AAG | GAC | GAG | TAT | GAA | CGA | CAT | AAC | AGC | TAT | ACC | TGT | 735 |
| Leu | Thr | Leu | Thr | Lys | Asp | Glu | Tyr | Glu | Arg | His | Asn | Ser | Tyr | Thr | Cys |
| | | | 205 | | | | | 210 | | | | | 215 | | |

| GAG | GCC | ACT | CAC | AAG | ACT | TCA | ACT | TCA | CCC | ATT | GTC | AAG | AGC | TTC | AAC | 783 |
| Glu | Ala | Thr | His | Lys | Thr | Ser | Thr | Ser | Pro | Ile | Val | Lys | Ser | Phe | Asn |
| | | | 220 | | | | | 225 | | | | | 230 | | |

| AGG | AAT | GAG | TGT | TAA | TAGCAAGGAG | ACAGTCATA | ATG | AAA | TAC | CTA | TTG | CCT | 835 |
| Arg | Asn | Glu | Cys | | | | Met | Lys | Tyr | Leu | Leu | Pro |
| | | 235 | | | | | 1 | | | | 5 | |

| ACG | GCA | GCC | GTT | GGA | TTG | TTA | TTA | CTC | GCG | GCC | CAA | CCG | GCC | ATG | GCC | 883 |
| Thr | Ala | Ala | Val | Gly | Leu | Leu | Leu | Leu | Ala | Ala | Gln | Pro | Ala | Met | Ala |
| | | | | 10 | | | | | 15 | | | | | 20 | |

| GAG | GTT | CAG | CTT | CAG | CAG | TCT | GGG | GCA | GAG | CTT | GTG | AAG | CCA | GGG | GCC | 931 |
| Glu | Val | Gln | Leu | Gln | Gln | Ser | Gly | Ala | Glu | Leu | Val | Lys | Pro | Gly | Ala |
| | | 25 | | | | | 30 | | | | | 35 | | | |

| TCA | GTC | AAG | TTG | TCC | TGC | ACA | GCT | TCT | GGC | TTC | AAC | ATT | AAA | GAC | ACC | 979 |
| Ser | Val | Lys | Leu | Ser | Cys | Thr | Ala | Ser | Gly | Phe | Asn | Ile | Lys | Asp | Thr |
| | 40 | | | | | 45 | | | | | 50 | | | | |

| TTT | ATG | CAC | TGG | GTG | AAG | CAG | AGG | CCT | GAA | CAG | GGC | CTG | GAG | TGG | ATT | 1027 |
| Phe | Met | His | Trp | Val | Lys | Gln | Arg | Pro | Glu | Gln | Gly | Leu | Glu | Trp | Ile |
| 55 | | | | 60 | | | | | 65 | | | | | 70 | |

| GGA | AGG | ATT | GAT | CCT | GCG | AAT | GGG | AAT | ACT | GAA | TAT | GAC | CCG | AAG | TTC | 1075 |
| Gly | Arg | Ile | Asp | Pro | Ala | Asn | Gly | Asn | Thr | Glu | Tyr | Asp | Pro | Lys | Phe |
| | | | | 75 | | | | | 80 | | | | | 85 | |

```
CAG GGC AAG GCC ACT ATA ACA GCA GAC ACA TCC TCC AAC ACA GTC AAC        1123
Gln Gly Lys Ala Thr Ile Thr Ala Asp Thr Ser Ser Asn Thr Val Asn
                90                  95                 100

CTG CAG CTC AGC AGC CTG ACA TCT GAG GAC ACT GCC GTC TAT TAC TGT        1171
Leu Gln Leu Ser Ser Leu Thr Ser Glu Asp Thr Ala Val Tyr Tyr Cys
               105                 110                 115

GCT AGT GGA GGG GAA CTG GGG TTT CCT TAC TGG GGC CAA GGG ACT CTG        1219
Ala Ser Gly Gly Glu Leu Gly Phe Pro Tyr Trp Gly Gln Gly Thr Leu
           120                 125                 130

GTC ACT GTC TCT GCA GCC AAA ACG ACA CCC CCA TCT GTC TAT CCA CTG        1267
Val Thr Val Ser Ala Ala Lys Thr Thr Pro Pro Ser Val Tyr Pro Leu
135             140                 145                 150

GCC CCT GGA TCT GCT GCC CAA ACT AAC TCC ATG GTG ACC CTG GGA TGC        1315
Ala Pro Gly Ser Ala Ala Gln Thr Asn Ser Met Val Thr Leu Gly Cys
                155                 160                 165

CTG GTC AAG GGC TAT TTC CCT GAG CCA GTG ACA GTG ACC TGG AAC TCT        1363
Leu Val Lys Gly Tyr Phe Pro Glu Pro Val Thr Val Thr Trp Asn Ser
           170                 175                 180

GGA TCC CTG TCC AGC GGT GTG CAC ACC TTC CCA GCT GTC CTG CAG TCT        1411
Gly Ser Leu Ser Ser Gly Val His Thr Phe Pro Ala Val Leu Gln Ser
                185                 190                 195

GAC CTC TAC ACT CTG AGC AGC TCA GTG ACT GTC CCC TCC AGC ACC TGG        1459
Asp Leu Tyr Thr Leu Ser Ser Ser Val Thr Val Pro Ser Ser Thr Trp
200                 205                 210

CCC AGC GAG ACC GTC ACC TGC AAC GTT GCC CAC CCG GCC AGC AGC ACC        1507
Pro Ser Glu Thr Val Thr Cys Asn Val Ala His Pro Ala Ser Ser Thr
215                 220                 225                 230

AAG GTG GAC AAG AAA ATT GTG CCC AGG GAT TGT ACT AGT GGA GGT GGA        1555
Lys Val Asp Lys Lys Ile Val Pro Arg Asp Cys Thr Ser Gly Gly Gly
                235                 240                 245

GGT AGC CAC CAT CAC CAT CAC CAT TAA TCTAGAGTTA AGCGGCCGTC              1602
Gly Ser His His His His His His
           250

GAGGGGGCCC CGATACCCAA TTCGCCTTAT                                       1632
```

(2) INFORMATION FOR SEQ ID NO:9:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:9:

```
Met Lys Tyr Leu Leu Pro Thr Ala Ala Ala Gly Leu Leu Leu Leu Ala
  1               5                  10                  15

Ala Gln Pro Ala Met Ala Asp Ile Gln Met Thr Gln Ser Pro Ala Ser
                 20                  25                  30

Leu Ser Ala Ser Val Gly Glu Thr Val Thr Ile Thr Cys Arg Ala Ser
             35                  40                  45

Gly Asn Ile His Asn Tyr Leu Ala Trp Tyr Gln Gln Lys Gln Gly Lys
         50                  55                  60

Ser Pro Gln Leu Leu Val Tyr Asn Ala Lys Thr Leu Ala Asp Gly Val
 65                  70                  75                  80

Pro Ser Arg Phe Ser Gly Ser Gly Ser Gly Thr Gln Tyr Ser Leu Lys
                 85                  90                  95

Ile Asn Ser Leu Gln Pro Glu Asp Phe Gly Ser Tyr Tyr Cys Gln His
            100                 105                 110
```

```
Phe Trp Ser Thr Pro Trp Thr Phe Gly Gly Gly Thr Lys Leu Glu Ile
            115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
                180                 185                 190

Ser Thr Tyr Ser Met Ser Ser Thr Leu Thr Leu Thr Lys Asp Glu Tyr
                195                 200                 205

Glu Arg His Asn Ser Tyr Thr Cys Glu Ala Thr His Lys Thr Ser Thr
210                 215                 220

Ser Pro Ile Val Lys Ser Phe Asn Arg Asn Glu Cys
225                 230                 235

(2) INFORMATION FOR SEQ ID NO:10:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO:10:

Met Lys Tyr Leu Leu Pro Thr Ala Ala Val Gly Leu Leu Leu Leu Ala
  1               5                  10                  15

Ala Gln Pro Ala Met Ala Glu Val Gln Leu Gln Gln Ser Gly Ala Glu
                 20                  25                  30

Leu Val Lys Pro Gly Ala Ser Val Lys Leu Ser Cys Thr Ala Ser Gly
             35                  40                  45

Phe Asn Ile Lys Asp Thr Phe Met His Trp Val Lys Gln Arg Pro Glu
         50                  55                  60

Gln Gly Leu Glu Trp Ile Gly Arg Ile Asp Pro Ala Asn Gly Asn Thr
 65                  70                  75                  80

Glu Tyr Asp Pro Lys Phe Gln Gly Lys Ala Thr Ile Thr Ala Asp Thr
                 85                  90                  95

Ser Ser Asn Thr Val Asn Leu Gln Leu Ser Ser Leu Thr Ser Glu Asp
            100                 105                 110

Thr Ala Val Tyr Tyr Cys Ala Ser Gly Gly Glu Leu Gly Phe Pro Tyr
            115                 120                 125

Trp Gly Gln Gly Thr Leu Val Thr Val Ser Ala Ala Lys Thr Thr Pro
130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
                180                 185                 190

Pro Ala Val Leu Gln Ser Asp Leu Tyr Thr Leu Ser Ser Ser Val Thr
                195                 200                 205

Val Pro Ser Ser Thr Trp Pro Ser Glu Thr Val Thr Cys Asn Val Ala
            210                 215                 220

His Pro Ala Ser Ser Thr Lys Val Asp Lys Lys Ile Val Pro Arg Asp
225                 230                 235                 240
```

```
Cys Thr Ser Gly Gly Gly Gly Ser His His His His His
              245                 250

(2) INFORMATION FOR SEQ ID NO:11:

(i) SEQUENCE CHARACTERISTICS:
        (A) LENGTH: 1644 base pairs
        (B) TYPE: nucleic acid
        (C) STRANDEDNESS: double
        (D) TOPOLOGY: Not Relevant (ii) MOLECULE TYPE: cDNA (iii) HYPOTHETICAL: NO (iv) ANTI-SENSE: NO (vi) ORIGINAL SOURCE:
        (A) ORGANISM: Mus musculus
        (B) STRAIN: BALB/c (vii) IMMEDIATE SOURCE:
        (B) CLONE: pHist22

(ix) FEATURE:
        (A) NAME/KEY: CDS
        (B) LOCATION: 88..798
        (D) OTHER INFORMATION: /product= "antibody fragment, Light
            Chain"
            /label= BotFab 22

(ix) FEATURE:
        (A) NAME/KEY: CDS
        (B) LOCATION: 818..1582
        (D) OTHER INFORMATION: /product= "antibody fragment, Heavy
            Chain"
            /label= BotFab 22

(xi) SEQUENCE DESCRIPTION: SEQ ID NO:11:
```

```
TATACGCCAA GCTCGAAATT AACCCTCACT AAAGGGAACA AAAGCTGGAG CTTGAATTCT        60

TAACTACTCG CCAAGGAGAC AGTCATA ATG AAA TAC CTA TTG CCT ACG GCG          111
                              Met Lys Tyr Leu Leu Pro Thr Ala
                                1               5

GCC GCT GGA TTG TTA TTA CTC GCT GCC CAA CCA GCC ATG GCC GAC ATC        159
Ala Ala Gly Leu Leu Leu Leu Ala Ala Gln Pro Ala Met Ala Asp Ile
         10                  15                  20

CAG ATG ACC CAG TCT CCA GCC TCC CTA TCT GCA TCT GTG GGA GAA ACT        207
Gln Met Thr Gln Ser Pro Ala Ser Leu Ser Ala Ser Val Gly Glu Thr
 25              30                  35                  40

GTC ACT ATC ACA TGT CGA GCA AGT GGG AAT ATT CAC AAT TAT TTA GCA        255
Val Thr Ile Thr Cys Arg Ala Ser Gly Asn Ile His Asn Tyr Leu Ala
                 45                  50                  55

TGG TAT CAG CAG AAA CAG GGA AAA TCT CCT CAG CTC CTG GTC TAT AAT        303
Trp Tyr Gln Gln Lys Gln Gly Lys Ser Pro Gln Leu Leu Val Tyr Asn
             60                  65                  70

GCA AAA ACC TTA GCA GAT GGT GTG CCA TCA AGG TTC AGT GGC AGT GGA        351
Ala Lys Thr Leu Ala Asp Gly Val Pro Ser Arg Phe Ser Gly Ser Gly
         75                  80                  85

TCA GGA ACA CAA TAT TCT CTC AAG ATC AAC AGC CTG CAG CCT GAA GAT        399
Ser Gly Thr Gln Tyr Ser Leu Lys Ile Asn Ser Leu Gln Pro Glu Asp
     90                  95                 100

TTT GGG AGT TAT TAC TGT CAA CAT TTT TGG AGT ACT CCG TGG ACG TTC        447
Phe Gly Ser Tyr Tyr Cys Gln His Phe Trp Ser Thr Pro Trp Thr Phe
105                 110                 115                 120

GGT GGA GGC ACC AAG CTG GAA ATC AAA CGG GCT GAT GCT GCA CCA ACT        495
Gly Gly Gly Thr Lys Leu Glu Ile Lys Arg Ala Asp Ala Ala Pro Thr
                125                 130                 135
```

```
GTA TCC ATC TTC CCA CCA TCC AGT GAG CAG TTA ACA TCT GGA GGT GCC      543
Val Ser Ile Phe Pro Pro Ser Ser Glu Gln Leu Thr Ser Gly Gly Ala
            140                 145                 150

TCA GTC GTG TGC TTC TTG AAC AAC TTC TAC CCC AAA GAC ATC AAT GTC      591
Ser Val Val Cys Phe Leu Asn Asn Phe Tyr Pro Lys Asp Ile Asn Val
            155                 160                 165

AAG TGG AAG ATT GAT GGC AGT GAA CGA CAA AAT GGC GTC CTG AAC AGT      639
Lys Trp Lys Ile Asp Gly Ser Glu Arg Gln Asn Gly Val Leu Asn Ser
170                 175                 180

TGG ACT GAT CAG GAC AGC AAA GAC AGC ACC TAC AGC ATG AGC AGC ACC      687
Trp Thr Asp Gln Asp Ser Lys Asp Ser Thr Tyr Ser Met Ser Ser Thr
185                 190                 195                 200

CTC ACA TTG ACC AAG GAC GAG TAT GAA CGA CAT AAC AGC TAT ACC TGT      735
Leu Thr Leu Thr Lys Asp Glu Tyr Glu Arg His Asn Ser Tyr Thr Cys
            205                 210                 215

GAG GCC ACT CAC AAG ACA TCA ACT TCA CCC ATT GTC AAG AGC TTC AAC      783
Glu Ala Thr His Lys Thr Ser Thr Ser Pro Ile Val Lys Ser Phe Asn
            220                 225                 230

AGG AAT GAG TGT TAA TAGCAAGGAG ACAGTCATA ATG AAA TAC CTA TTG CCT     835
Arg Asn Glu Cys                          Met Lys Tyr Leu Leu Pro
            235                           1               5

ACG GCA GCC GCT GGA TTG TTA TTA CTC GCG GCC CAA CCG GCC ATG GCC      883
Thr Ala Ala Ala Gly Leu Leu Leu Leu Ala Ala Gln Pro Ala Met Ala
            10                  15                  20

GAG GTT CAG CTT CAG CAG TCT GGG GCA GAG CTT GTG AAG CCA GGG GCC      931
Glu Val Gln Leu Gln Gln Ser Gly Ala Glu Leu Val Lys Pro Gly Ala
            25                  30                  35

TCA GTC AAG TTG TCC TGC ACA GCT TCT GGC TTC AAC ATT AAA GAC ACC      979
Ser Val Lys Leu Ser Cys Thr Ala Ser Gly Phe Asn Ile Lys Asp Thr
            40                  45                  50

TTT ATG CAC TGG GTG AAG CAG AGG CCT GAA CAG GGC CTG GAG TGG ATT     1027
Phe Met His Trp Val Lys Gln Arg Pro Glu Gln Gly Leu Glu Trp Ile
55                  60                  65                  70

GGA AGG ATT GAT CCT GCG AAT GGG AAT ACT GAA TAT GAC CCG AAG TTC     1075
Gly Arg Ile Asp Pro Ala Asn Gly Asn Thr Glu Tyr Asp Pro Lys Phe
            75                  80                  85

CAG GGC AAG GCC ACT ATA ACA GCA GAC ACA TCC TCC AAC ACA GTC AAC     1123
Gln Gly Lys Ala Thr Ile Thr Ala Asp Thr Ser Ser Asn Thr Val Asn
            90                  95                  100

CTG CAG CTC AGC AGC CTG ACA TCT GAG GAC ACT GCC GTC TAT TAC TGT     1171
Leu Gln Leu Ser Ser Leu Thr Ser Glu Asp Thr Ala Val Tyr Tyr Cys
            105                 110                 115

GCT AGT GGA GGG GAA CTG GGG TTT CCT TAC TGG GGC CAA GGG ACT CTG     1219
Ala Ser Gly Gly Glu Leu Gly Phe Pro Tyr Trp Gly Gln Gly Thr Leu
            120                 125                 130

GTC ACT GTC TCT GCA GCC AAA ACG ACA CCC CCA TCT GTC TAT CCA CTG     1267
Val Thr Val Ser Ala Ala Lys Thr Thr Pro Pro Ser Val Tyr Pro Leu
135                 140                 145                 150

GCC CCT GGA TCT GCT GCC CAA ACT AAC TCC ATG GTG ACC CTG GGA TGC     1315
Ala Pro Gly Ser Ala Ala Gln Thr Asn Ser Met Val Thr Leu Gly Cys
            155                 160                 165

CTG GTC AAG GGC TAC TTC CCT GAG CCA GTG ACA GTG ACC TGG AAC TCT     1363
Leu Val Lys Gly Tyr Phe Pro Glu Pro Val Thr Val Thr Trp Asn Ser
            170                 175                 180

GGA TCC CTG TCC AGC GGT GTG CAC ACC TTC CCA GCT GTC CTG CAG TCT     1411
Gly Ser Leu Ser Ser Gly Val His Thr Phe Pro Ala Val Leu Gln Ser
            185                 190                 195

GAC CTC TAC ACT CTG AGC AGC TCA GTG ACT GTC CCC TCC AGC ACC TGG     1459
Asp Leu Tyr Thr Leu Ser Ser Ser Val Thr Val Pro Ser Ser Thr Trp
            200                 205                 210
```

```
CCC AGT GAG ACC GTC ACC TGC AAC GTT GCC CAC CCG GCC AGC AGC ACC       1507
Pro Ser Glu Thr Val Thr Cys Asn Val Ala His Pro Ala Ser Ser Thr
215                 220                 225                 230

AAG GTG GAC AAG AAA ATT GTG CCC AGG GAT TGT ACT AGT GGA GGT GGA       1555
Lys Val Asp Lys Lys Ile Val Pro Arg Asp Cys Thr Ser Gly Gly Gly
                235                 240                 245

GGT AGC CAC CAT CAC CAT CAC CAT TAA TCTAGAGTTA AGCGGCCGTC             1602
Gly Ser His His His His His His
                250

GAGGGGGGGC CGGTACCCA ATTCGCCCTA TAGTGAGTCG TA                         1644
```

(2) INFORMATION FOR SEQ ID NO:12:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:12:

```
Met Lys Tyr Leu Leu Pro Thr Ala Ala Ala Gly Leu Leu Leu Leu Ala
 1               5                  10                  15

Ala Gln Pro Ala Met Ala Asp Ile Gln Met Thr Gln Ser Pro Ala Ser
                20                  25                  30

Leu Ser Ala Ser Val Gly Glu Thr Val Thr Ile Thr Cys Arg Ala Ser
            35                  40                  45

Gly Asn Ile His Asn Tyr Leu Ala Trp Tyr Gln Gln Lys Gln Gly Lys
        50                  55                  60

Ser Pro Gln Leu Leu Val Tyr Asn Ala Lys Thr Leu Ala Asp Gly Val
65                  70                  75                  80

Pro Ser Arg Phe Ser Gly Ser Gly Ser Gly Thr Gln Tyr Ser Leu Lys
                85                  90                  95

Ile Asn Ser Leu Gln Pro Glu Asp Phe Gly Ser Tyr Tyr Cys Gln His
            100                 105                 110

Phe Trp Ser Thr Pro Trp Thr Phe Gly Gly Gly Thr Lys Leu Glu Ile
        115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
210                 215                 220

Ser Pro Ile Val Lys Ser Phe Asn Arg Asn Glu Cys
225                 230                 235
```

(2) INFORMATION FOR SEQ ID NO:13:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO:13:

```
Met Lys Tyr Leu Leu Pro Thr Ala Ala Ala Gly Leu Leu Leu Leu Ala
 1               5                  10                  15
Ala Gln Pro Ala Met Ala Glu Val Gln Leu Gln Gln Ser Gly Ala Glu
             20                  25                  30
Leu Val Lys Pro Gly Ala Ser Val Lys Leu Ser Cys Thr Ala Ser Gly
         35                  40                  45
Phe Asn Ile Lys Asp Thr Phe Met His Trp Val Lys Gln Arg Pro Glu
     50                  55                  60
Gln Gly Leu Glu Trp Ile Gly Arg Ile Asp Pro Ala Asn Gly Asn Thr
 65                  70                  75                  80
Glu Tyr Asp Pro Lys Phe Gln Gly Lys Ala Thr Ile Thr Ala Asp Thr
             85                  90                  95
Ser Ser Asn Thr Val Asn Leu Gln Leu Ser Ser Leu Thr Ser Glu Asp
             100                 105                 110
Thr Ala Val Tyr Tyr Cys Ala Ser Gly Gly Glu Leu Gly Phe Pro Tyr
             115                 120                 125
Trp Gly Gln Gly Thr Leu Val Thr Val Ser Ala Ala Lys Thr Thr Pro
     130                 135                 140
Pro Ser Val Tyr Pro Leu Ala Pro Gly Ser Ala Ala Gln Thr Asn Ser
145                 150                 155                 160
Met Val Thr Leu Gly Cys Leu Val Lys Gly Tyr Phe Pro Glu Pro Val
             165                 170                 175
Thr Val Thr Trp Asn Ser Gly Ser Leu Ser Ser Gly Val His Thr Phe
             180                 185                 190
Pro Ala Val Leu Gln Ser Asp Leu Tyr Thr Leu Ser Ser Ser Val Thr
     195                 200                 205
Val Pro Ser Ser Thr Trp Pro Ser Glu Thr Val Thr Cys Asn Val Ala
     210                 215                 220
His Pro Ala Ser Ser Thr Lys Val Asp Lys Lys Ile Val Pro Arg Asp
225                 230                 235                 240
Cys Thr Ser Gly Gly Gly Ser His His His His His His
             245                 250
```